US011801089B2

(12) United States Patent
Montague et al.

(10) Patent No.: US 11,801,089 B2
(45) Date of Patent: Oct. 31, 2023

(54) CAUTERIZING DEVICE FOR USE WITH STENTS

(71) Applicant: BOSTON SCIENTIFIC SCIMED, INC., Maple Grove, MN (US)

(72) Inventors: Matthew Montague, Galway (IE); Louis McNern, Donegal (IE); Geraldine Toner, Raphoe (IE); Martyn G. Folan, Galway (IE); Gary Gilmartin, Mayo (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1198 days.

(21) Appl. No.: 16/417,338

(22) Filed: May 20, 2019

(65) Prior Publication Data

US 2019/0350645 A1    Nov. 21, 2019

Related U.S. Application Data

(60) Provisional application No. 62/674,564, filed on May 21, 2018.

(51) Int. Cl.
| | |
|---|---|
| *A61B 18/14* | (2006.01) |
| *A61M 25/00* | (2006.01) |
| *A61B 18/00* | (2006.01) |
| *A61F 2/04* | (2013.01) |
| *A61F 2/95* | (2013.01) |

(52) U.S. Cl.
CPC ............ *A61B 18/1482* (2013.01); *A61F 2/04* (2013.01); *A61F 2/95* (2013.01); *A61M 25/0082* (2013.01); *A61B 2018/00595* (2013.01); *A61F 2002/041* (2013.01)

(58) Field of Classification Search
CPC ...... A61B 18/1482; A61B 2018/00595; A61B 2018/00529; A61B 2090/065; A61B 18/1492; A61F 2/04; A61F 2/95; A61F 2002/041; A61M 25/0082
See application file for complete search history.

(56) References Cited

U.S. PATENT DOCUMENTS

| | | | |
|---|---|---|---|
| 5,429,636 A | 7/1995 | Shikhman et al. | |
| 5,599,347 A * | 2/1997 | Hart ...................... | A61M 13/00 606/41 |
| 6,015,405 A | 1/2000 | Schwartz et al. | |
| 6,620,122 B2 | 9/2003 | Stinson et al. | |
| (Continued) | | | |

FOREIGN PATENT DOCUMENTS

WO      2009070837 A1     6/2009

OTHER PUBLICATIONS

International Search Report and Written Opinion dated Aug. 26, 2019 for International Application No. PCT/US2019/033153.

*Primary Examiner* — Linda C Dvorak
*Assistant Examiner* — Mystee Nguyen Delgado
(74) *Attorney, Agent, or Firm* — Seager, Tufte & Wickhem, LLP

(57) ABSTRACT

A lumen-apposing access system may include a catheter and a cauterization tip. The cauterization tip may include a biasing member and a cautery element. The cauterization tip may move relative to the catheter between a first position in which the cautery element is electrically inactive, and a second position in which the cautery element is electrically active. The biasing member biases the cautery element in the first position.

15 Claims, 18 Drawing Sheets

(56) References Cited

U.S. PATENT DOCUMENTS

| | | | |
|---|---|---|---|
| 8,784,413 B2 * | 7/2014 | Govari | A61B 5/6843 606/41 |
| 9,888,926 B2 | 2/2018 | Phan et al. | |
| 2004/0098105 A1 | 5/2004 | Stinson et al. | |
| 2007/0191829 A1 * | 8/2007 | McGee | A61B 18/14 606/41 |
| 2009/0281379 A1 | 11/2009 | Binmoeller et al. | |
| 2013/0317500 A1 | 11/2013 | Scopton et al. | |

* cited by examiner

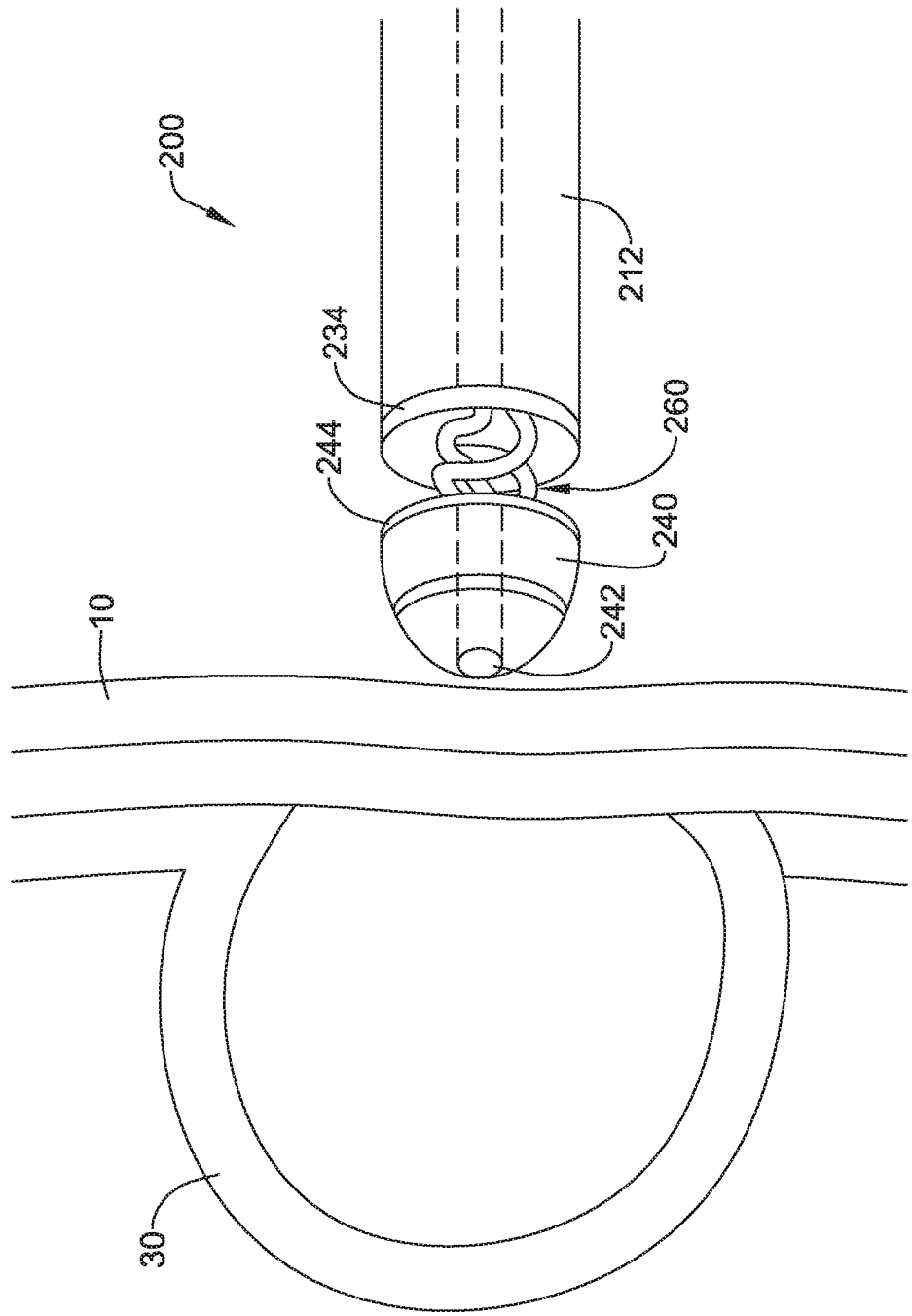

U.S. 11,801,089 B2

CAUTERIZING DEVICE FOR USE WITH STENTS

CROSS-REFERENCE TO RELATED APPLICATIONS

This application claims the benefit of priority under 35 U.S.C. § 119 of U.S. Provisional Application No. 62/674,564, filed May 21, 2018, the entire disclosure of which is hereby incorporated by reference.

TECHNICAL FIELD

The disclosure is directed to medical devices having cauterizing elements. More particularly, the disclosure is directed to catheter shafts including a selectively activatable cauterizing tip moveable between an inactive and an active state. The disclosure is also directed to methods of accessing a lumen through the lumen wall.

BACKGROUND

A pancreatic pseudocyst is a pancreatic fluid collection that occurs from chronic pancreatitis. Some pseudocysts resolve without treatment. When drainage is indicated, pseudocysts can be treated through surgical therapy (excision, external drainage or internal drainage), percutaneous therapy (percutaneous drainage) or endoscopic therapy (endoscopic drainage or endoscopic ultrasound (EUS)-guided endoscopic drainage). The EUS procedure, using a lumen-apposing self-expanding stent, may replace surgery and/or traditional endoscopic methods. A lumen-apposing self-expanding stent may also be used in the case of a failed endoscopic retrograde cholangio-pancreatography (ERCP) or malignant stricture. EUS replaces an external drain or a difficult, time consuming ERCP procedure. Gallstones are the most common biliary problem which can cause restricted bile flow and infection/inflammation. EUS provides an option for non-surgical candidates.

Lumen-apposing metal stents (LAMS) may be delivered using an electrocautery enhanced delivery system for use to facilitate transgastric or transduodenal endoscopic drainage of symptomatic pancreatic pseudocysts. In particular, pseudocysts 6 cm or greater in size and walled-off necrosis 6 cm or greater in size with 70% or greater fluid content that are adherent to the gastric or bowel wall may be treated using LAMS. The LAMS creates an anastomosis between two structures. Once placed, the stent functions as an access port allowing passage of standard therapeutic endoscopes to facilitate debridement, irrigation and cystoscopy. One example of a LAMS device is the AXIOS™ stent, sold by Boston Scientific Corp. of Marlborough, Mass.

In instances where the LAMS device is being placed as an access to a duct, the cross-sectional area of the duct may be relatively small. This may present problems involving accidental cauterization of the opposite duct wall, as there is little room for error when cauterizing. Therefore, a need remains for medical devices including cauterization catheters with more controlled activation of the cauterization tip.

SUMMARY

The disclosure is directed to several alternative designs, materials and methods of using medical device structures and assemblies.

An example includes a lumen-apposing access system comprising a catheter having a proximal end and a distal end, and a cauterization tip disposed on the distal end of the catheter, the cauterization tip having a proximal portion, a distal portion, and a biasing member, the distal portion including a cautery element, wherein the distal portion is moveable relative to the proximal portion between a first position in which the cautery element is electrically inactive, and a second position in which the cautery element is electrically active, wherein the biasing member biases the distal portion in the first position.

Alternatively or additionally to the above example, when in the first position, the distal portion is spaced apart from the proximal portion and when in the second position, the distal portion contacts the proximal portion.

Alternatively or additionally to any of the above examples, the cauterization tip includes an electrical circuit that is completed when the distal portion is in the second position, and the electrical circuit is broken when the distal portion is in the first position.

Alternatively or additionally to any of the above examples, a wire extends through the catheter from the proximal end to the proximal portion of the cauterization tip, wherein the distal portion has a contact surface that contacts the wire when the distal portion is in the second position, completing the electrical circuit, and is spaced apart from the wire when the distal portion is in the first position.

Alternatively or additionally to any of the above examples, the biasing member is a flexible bridge disposed between the proximal portion and distal portion of the cauterization tip.

Alternatively or additionally to any of the above examples, the flexible bridge is corrugated.

Alternatively or additionally to any of the above examples, the biasing member is a spring disposed between the proximal portion and distal portion of the cauterization tip.

Alternatively or additionally to any of the above examples, a proximal end of the distal portion and a distal end of the proximal portion include electrical contacts.

Alternatively or additionally to any of the above examples, the biasing member is a spring disposed at a distal end of the distal portion.

Alternatively or additionally to any of the above examples, the distal portion includes a proximal neck slidingly disposed within a lumen of the proximal portion.

Alternatively or additionally to any of the above examples, a first wire extends through the catheter from the proximal end to the proximal portion of the cauterization tip, wherein the distal portion has a second wire extending from a distal tip cautery surface into the proximal neck, wherein when the spring is in a relaxed state and the distal portion is in the first position, the second wire is spaced apart from the first wire, wherein when the spring is compressed and the distal portion is in the second position, the second wire contacts the first wire, completing an electrical circuit between the first wire and the second wire.

Alternatively or additionally to any of the above examples, the biasing member is a spring disposed at a distal end of the distal portion, wherein the distal portion includes a proximal neck slidingly disposed within a lumen of the proximal portion, wherein a first wire extends through the catheter from the proximal end to the proximal portion of the cauterization tip, wherein the distal portion has a second wire extending from a distal tip cautery surface into the proximal neck, wherein the biasing member includes a first magnet disposed on a distal region of the first wire and a second magnet disposed on a proximal region of the second wire, wherein the first magnet and the second magnet are oriented to repel one another when in close proximity, thereby biasing the distal portion in the first position, wherein when the distal portion is in the second position, the second wire contacts the first wire, completing an electrical circuit between the first wire and the second wire.

Alternatively or additionally to any of the above examples, the biasing member is a gas filled chamber disposed between the proximal portion and the distal portion.

Another example is a lumen-apposing access system comprising a catheter having a proximal end and a distal end, an inner shaft axially moveable within a lumen of the catheter, and a cauterization tip disposed on a distal end of the inner shaft, the cauterization tip having a proximal portion, a distal portion, and a biasing member, the distal portion extending distal of the distal end of the catheter and including a cautery element, wherein the distal portion is moveable relative to the proximal portion between a first position in which the distal portion is spaced apart from the proximal portion and the cautery element is electrically inactive, and a second position in which the distal portion contacts the proximal portion and the cautery element is electrically active, wherein the biasing member biases the distal portion in the first position.

Alternatively or additionally to the above example, a wire extends along the inner shaft from the proximal end of the catheter to the proximal portion of the cauterization tip, wherein the distal portion has a contact surface that contacts the wire when the distal portion is in the second position, completing an electrical circuit, and is spaced apart from the wire when the distal portion is in the first position, breaking the electrical circuit.

Alternatively or additionally to any of the above examples, the biasing member is a flexible bridge disposed between the proximal portion and distal portion of the cauterization tip.

Alternatively or additionally to any of the above examples, the biasing member is a spring.

Another example is a method of accessing a lumen through a wall of the lumen, comprising advancing a distal end of a catheter to a lumen wall, the catheter including a cauterization tip disposed on the distal end of the catheter, the cauterization tip having a proximal portion, a distal portion, and a biasing member, the distal portion including a cautery element, wherein the distal portion is moveable relative to the proximal portion between a first position in which the distal portion is spaced apart from the proximal portion and the cautery element is electrically inactive, and a second position in which the distal portion contacts the proximal portion and the cautery element is electrically active, wherein the biasing member biases the distal portion in the first position. The method further includes pushing the cauterization tip against a first side of the lumen wall, thereby applying a proximally directed force onto the distal portion which moves the distal portion into contact with the proximal portion and activates the cautery element, and moving the cauterization tip through the lumen wall until the distal portion reaches a second side of the lumen wall, at which point the proximally directed force is removed and the biasing member moves the distal portion away from the proximal portion, into the first position, deactivating the cautery element.

Alternatively or additionally to the above example, moving the distal portion into the first position automatically deactivates the cautery element.

Alternatively or additionally to any of the above examples, the catheter includes a stent, the method further comprising expanding the stent across the lumen wall.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 5A is an illustration of the catheter of FIG. 4A adjacent a pseudocyst;

Figure 1:
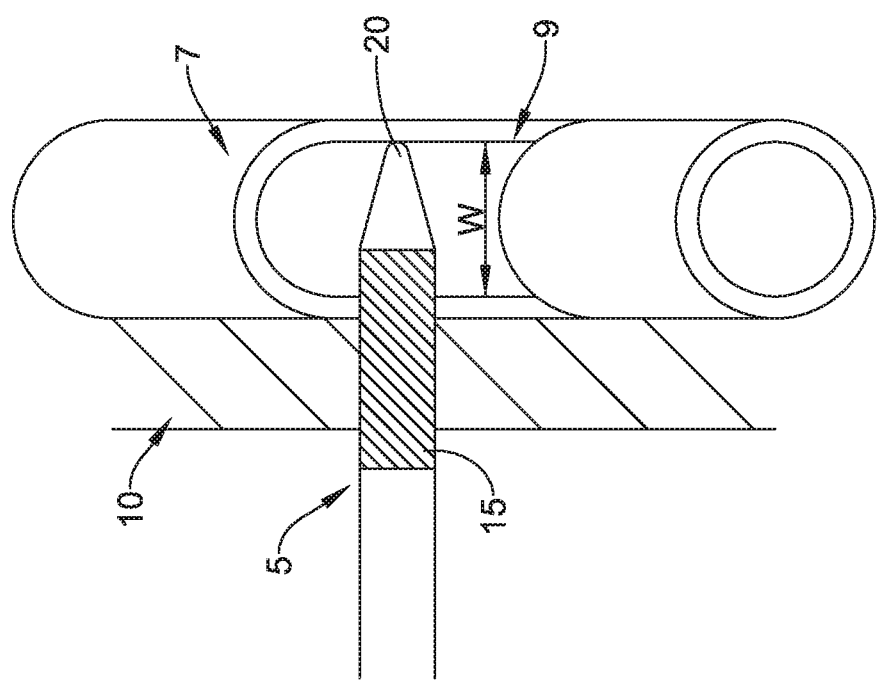
FIG. 1 is a perspective partial cut-away view of a prior art device in the common bile duct.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
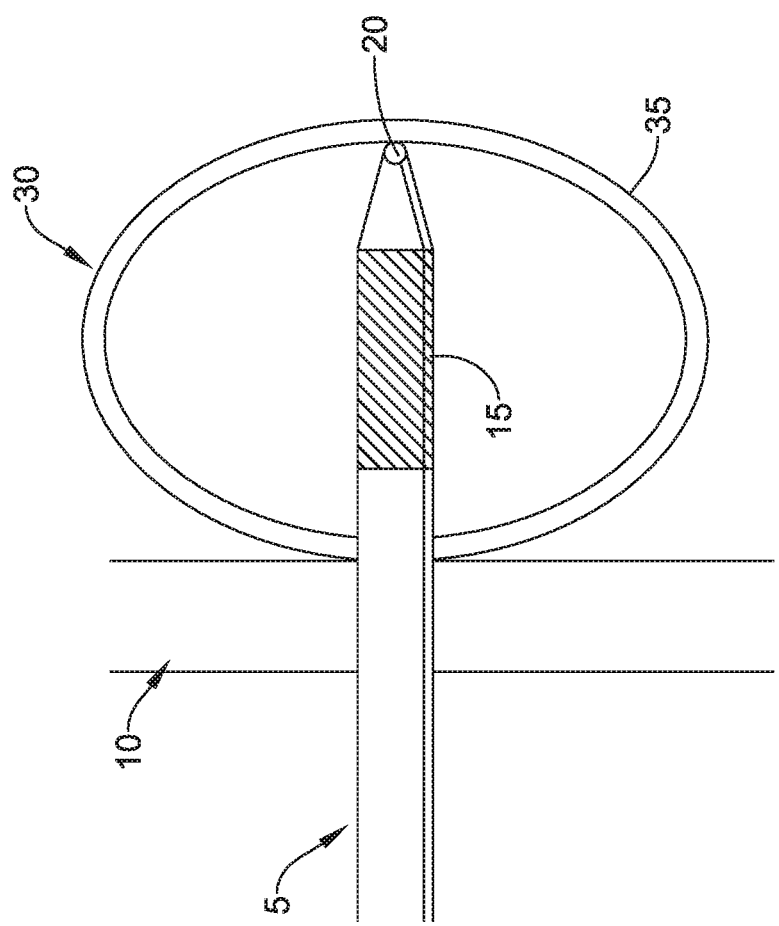
FIG. 2 is a cross-sectional view of a prior art device in a pseudocyst.

Referring to FIG. 1, there is shown a conventional prior art cauterization catheter 5 with a marker 15 disposed adjacent the distal cauterization tip 20. When the catheter 5 is used to create an opening through a tissue wall 10 and into a small lumen 7 such as the common bile duct, errors in the timing of turning off the cauterization power may result in injury to the back wall 9 of the lumen, i.e., the tissue wall of the body lumen opposite the entry point of the cauterization tip. Conventional cauterizing devices involve the manual activation of the cauterizing tip, such as with a pedal. If the operator doesn't release the cauterizing pedal in time, there is a risk of the device cauterizing through the opposite side of the duct wall. It may be difficult for the operator to know when to release the pedal due to visual interference (direct imaging and EUS imaging, and the ease with which the device can cauterize through the tissue wall, i.e. there is little resistance. Even when the catheter 5 is provided with a marker 15 adjacent the distal cauterization tip 20, the marker 15 may not provide the needed information regarding when to inactivate the cauterization tip 20 in the relatively small width W of the lumen 7. Additionally, the cauterization can be a blinded action due to temporary interference during activation of the cautery tip, especially during interaction with thicker walled vessels or pseudocysts, such as illustrated in FIG. 2. The relatively thick wall formed by the combined tissue wall 10 and pseudocyst 30 may provide greater resistance such that upon breaking through the tissue wall and into the pseudocyst 30, the catheter 5 and cauterization tip 20 moves quickly to the back wall 35, where injury may occur if the cauterization tip is not inactivated before contact. The marker 15 may not provide sufficient guidance to avoid contact of the cauterization tip 20 with the back wall 35.

Figure 3A:
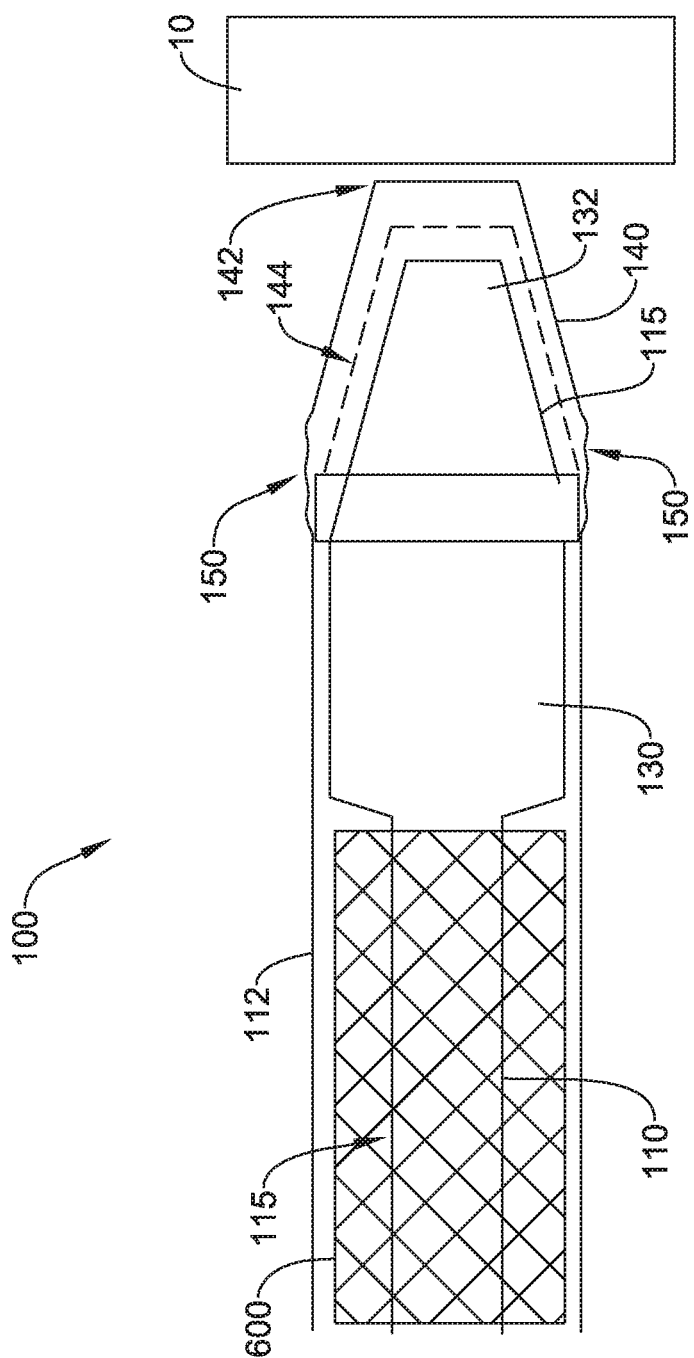
FIG. 3A is a cross-sectional view of an exemplary cauterization catheter in a first position adjacent a tissue wall.

Referring to FIG. 3A, there is shown an exemplary cauterization catheter 100 that includes a safety mechanism that provides the advantage of a more controlled cauterization. The catheter 100 may include an outer shaft 112 and an inner shaft 110 disposed within a lumen of the outer shaft 112. The catheter 100 may have a cautery tip disposed at a distal end thereof including a proximal cautery portion 130 and a distal cautery portion 140. The proximal cautery portion 130 may be fixed to the inner shaft 110 and an electrically conductive cautery wire 115 may extend along the inner shaft 110 from a proximal end of the inner shaft 110 to the proximal cautery portion 130. The cautery wire 115 may extend around the distal end 132 of the proximal cautery portion 130. The distal cautery portion 140 may be attached to the distal end of the outer shaft 112. In the example illustrated in FIGS. 3A-3C, the distal cautery portion 140 is connected to the outer shaft 112 by a biasing member 150. The distal cautery portion 140 may include a contact surface 144 that, when in contact with the cautery wire 115, completes an electrical circuit and activates a distal cautery surface 142 configured to cut tissue.

Figure 3B:
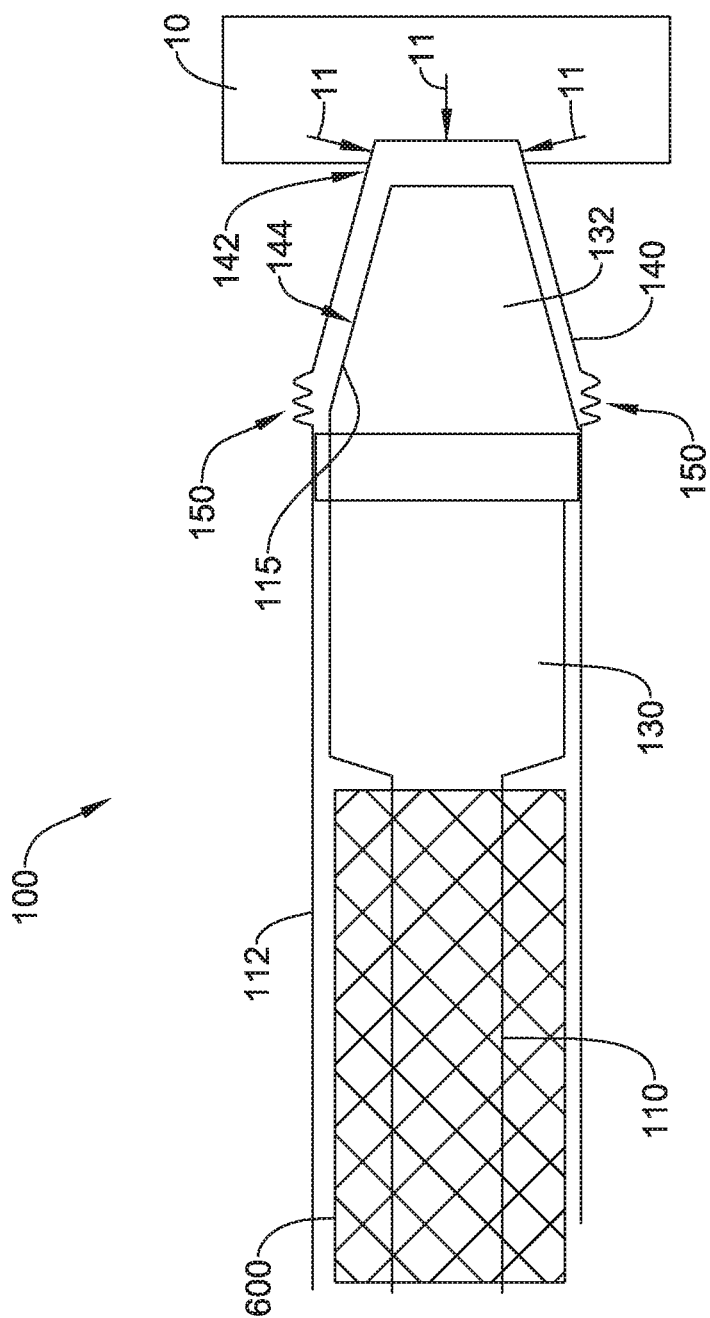
FIG. 3B is a cross-sectional view of the catheter of FIG. 3A in a second position disposed partially within the tissue wall.
Figure 3C:
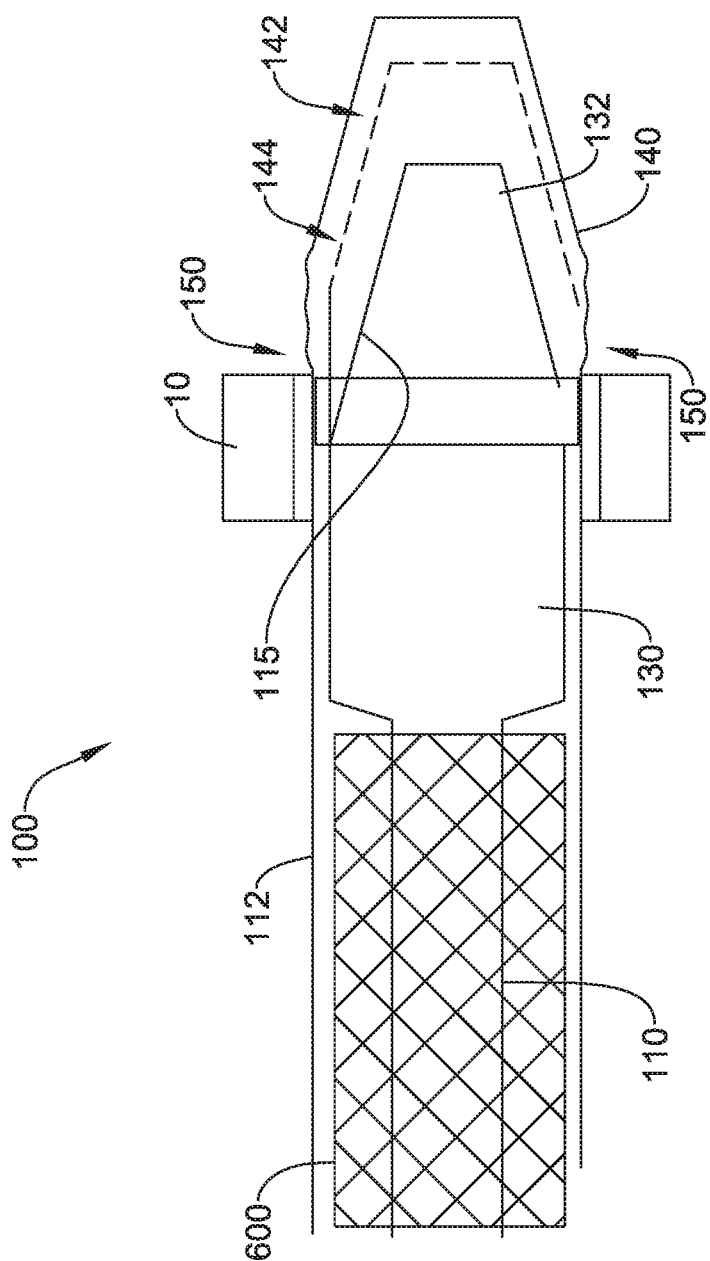
FIG. 3C is a cross-sectional view of the catheter of FIG. 3A in the first position extending through the tissue wall.

The cauterization catheter 100 shown in FIGS. 3A-3C may be used to deliver a stent 600 which may be a lumen-apposing metal stent (LAMS). The stent 600 may be disposed over the inner shaft 110 proximal of the proximal cautery portion 130, as shown in FIGS. 3A-3C.

The distal cautery portion 140 is configured to move between a first position and a second position relative to the proximal cautery portion 130. FIG. 3A illustrates the first position, with the distal cautery portion 140 spaced apart from the proximal cautery portion 130 and the contact surface 144 spaced apart from the cautery wire 115, breaking the electrical circuit and inactivating the cautery tip. FIG. 3B illustrates the second position, in which the catheter 100 has been pushed against the tissue wall 10, and the force indicated by arrows 11 causes the distal cautery portion 140 to contact the proximal cautery portion 130, with the contact surface 144 contacting the cautery wire 115, completing the electrical circuit and activating the cautery tip.

The biasing member 150 may provide the safety mechanism in that the biasing member 150 is configured to keep the distal cautery portion 140 in the first, inactive position unless a proximally directed force is applied to the distal cautery surface 142. The biasing member 150 may be a flexible bridge disposed between the distal end of the outer shaft 112 and the distal cautery portion 140. In the example illustrated in FIGS. 3A-3C, the biasing member 150 may be a corrugated element configured to compress when a proximally directed force is applied to the distal cautery surface 142. As the biasing member 150 compresses, the contact surface 144 of the distal cautery portion 140 moves into contact with the cautery wire 115 and completes the electrical connection to activate the distal cautery surface 142. The spaced apart contact surface 144 and cautery wire 115, along with the biasing member 150 provide the safety mechanism that only allows power to the distal cautery surface 142 at the tip of the catheter when the distal cautery surface 142 is being pushed through a tissue wall 10. The mechanism may be sensitive to a predetermined pressure experienced by the tip during cauterization. Once the distal cautery surface 142 passes through the tissue wall 10, as shown in FIG. 3C, the release in pressure causes the biasing member 150 to elongate, pushing the distal cautery portion 140 and contact surface 144 away from the proximal cautery portion 130 and the cautery wire 115, thereby breaking the electrical circuit and disconnecting power to the tip immediately. This rapid disconnection of power to the cautery surface 142 may eliminate the possibility of the user cauterizing through the opposite wall by mistake.

During conventional lumen-apposing stent placement, the operator tracks the device through the anatomy to the deployment location, as determined by EUS imaging. Once the device is at the desired location, the operator presses the cauterization foot pedal to initiate cauterization of the tissue. The device continues to cauterize until the operator releases the foot pedal. The conventional system relies on the operator releasing the foot pedal as the only means of stopping cauterization. The safety mechanism described above in catheter 100 introduces a continuous break to the cauterization circuit, as illustrated in FIG. 3A, with the circuit only being completed when the distal cautery portion 140 is pushed into contact with the proximal cautery portion 130 by the pressure exerted by the tissue wall 10 (FIG. 3B). Once the distal cautery portion 140 has passed through the tissue wall 10, the pressure is automatically released from the distal cautery portion 140, and the biasing member 150 returns to the elongated configuration, moving the contact surface 144 of the distal cautery portion 140 away from the cautery wire 115, breaking the circuit again (FIG. 3C). This automatic breaking of the circuit as soon as the distal cautery portion 140 passes through the tissue wall 10 may prevent accidental cauterization of tissue such as the opposing lumen or cyst wall.

Once the distal cautery portion 140 has passed through the tissue wall 10, and the cauterization has been stopped, the catheter 100 may be used to deliver a stent 600 across the tissue wall 10. As the catheter 100 is now in the first, inactive position, the catheter 100 may be maneuvered to place the stent 600 into position for deployment without concern that the distal cautery surface 142 may accidentally injure tissue of the back wall of the lumen or pseudocyst.

Figure 4A:
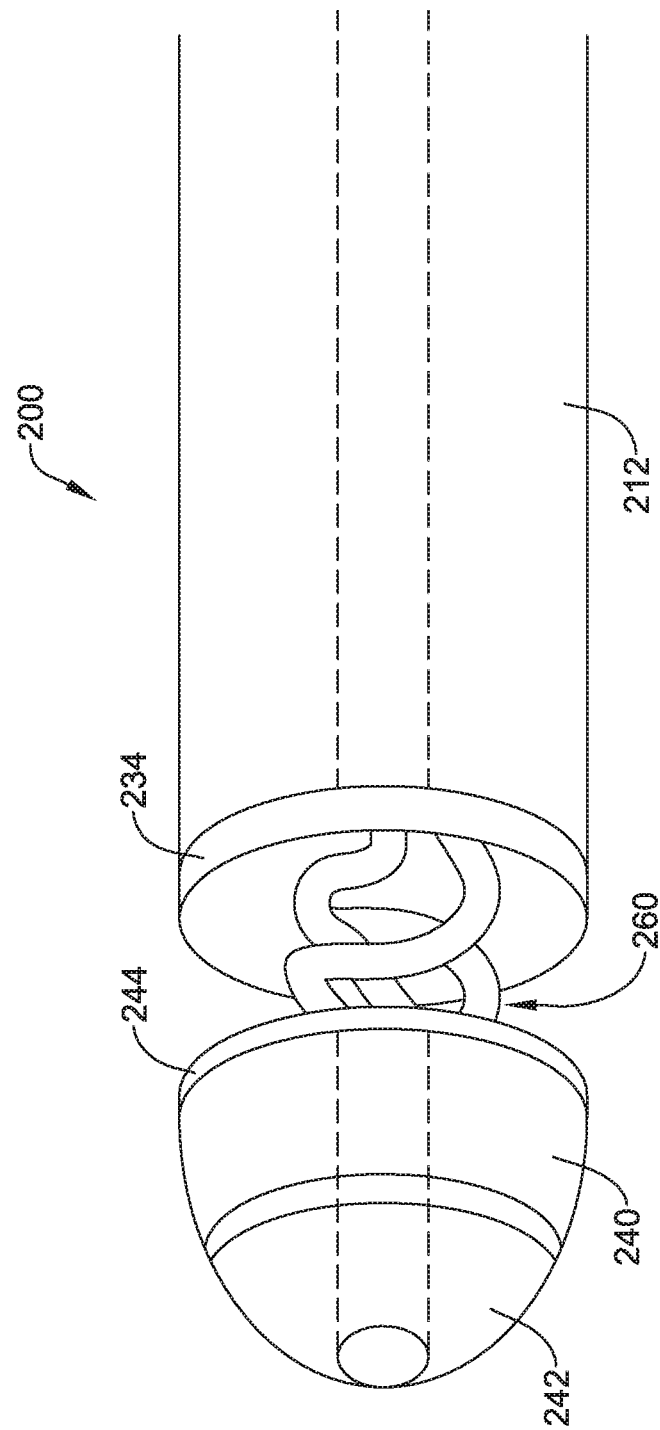
FIG. 4A is a perspective view of a second exemplary cauterization catheter in a first position.
Figure 4B:
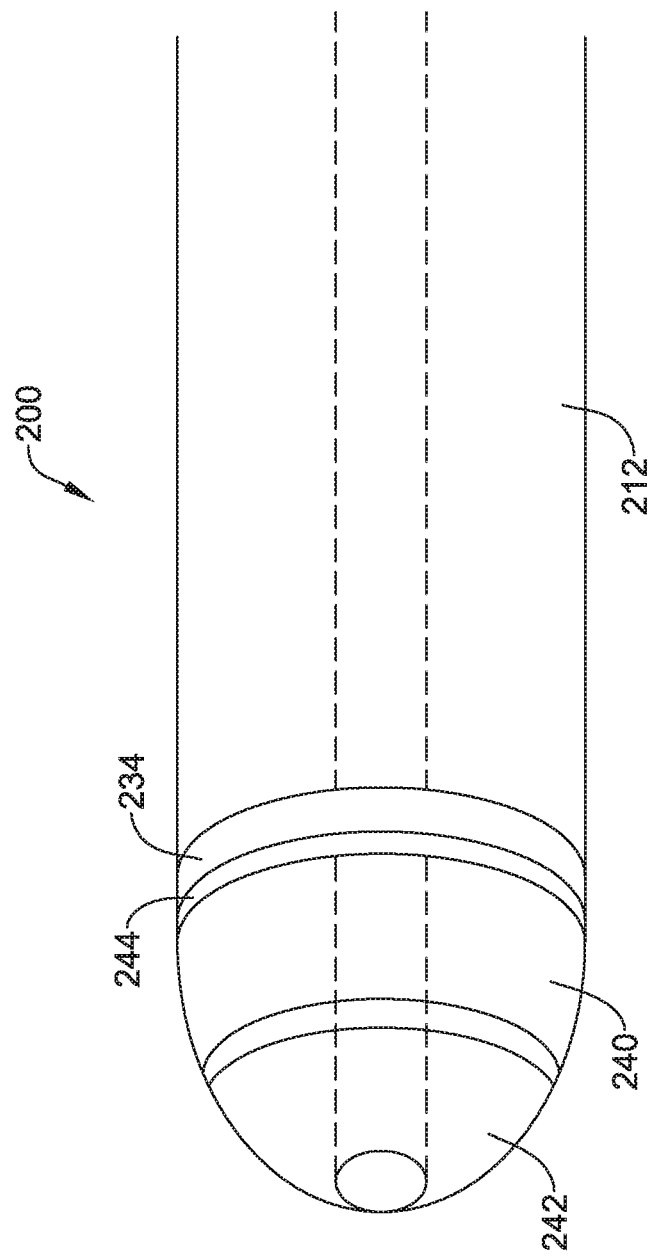
FIG. 4B is a perspective view of the catheter of FIG. 4A in a second position.

A further exemplary cauterization catheter 200 is illustrated in FIGS. 4A and 4B. The cauterization catheter 200 includes a catheter shaft 212 having a first electrical contact surface 234 on a distal end thereof and a distal tip portion 240 attached to the catheter shaft 212 by a spring 260. An electrical wire (not shown) extends through the catheter shaft 212 from a proximal end thereof to the first electrical contact surface 234. The distal tip portion 240 may include a second electrical contact surface 244 at a proximal end thereof, electrically connected to a distal cautery surface 242. The spring 260 biases the distal tip portion 240 away from the catheter shaft 212 in the first, inactive position, as shown in FIG. 4A. In the first position the first and second electrical contact surfaces 234, 244 are biased apart, breaking the electrical circuit. A proximally directed force exerted on the distal tip portion 240 compresses the spring 260 and moves the distal tip portion 240 proximally until the second contact surface 244 contacts the first contact surface 234, thereby completing the circuit, as shown in FIG. 4B. In this second position the distal cautery surface 242 is activated, allowing the surface to cut through tissue.

Figure 5B:
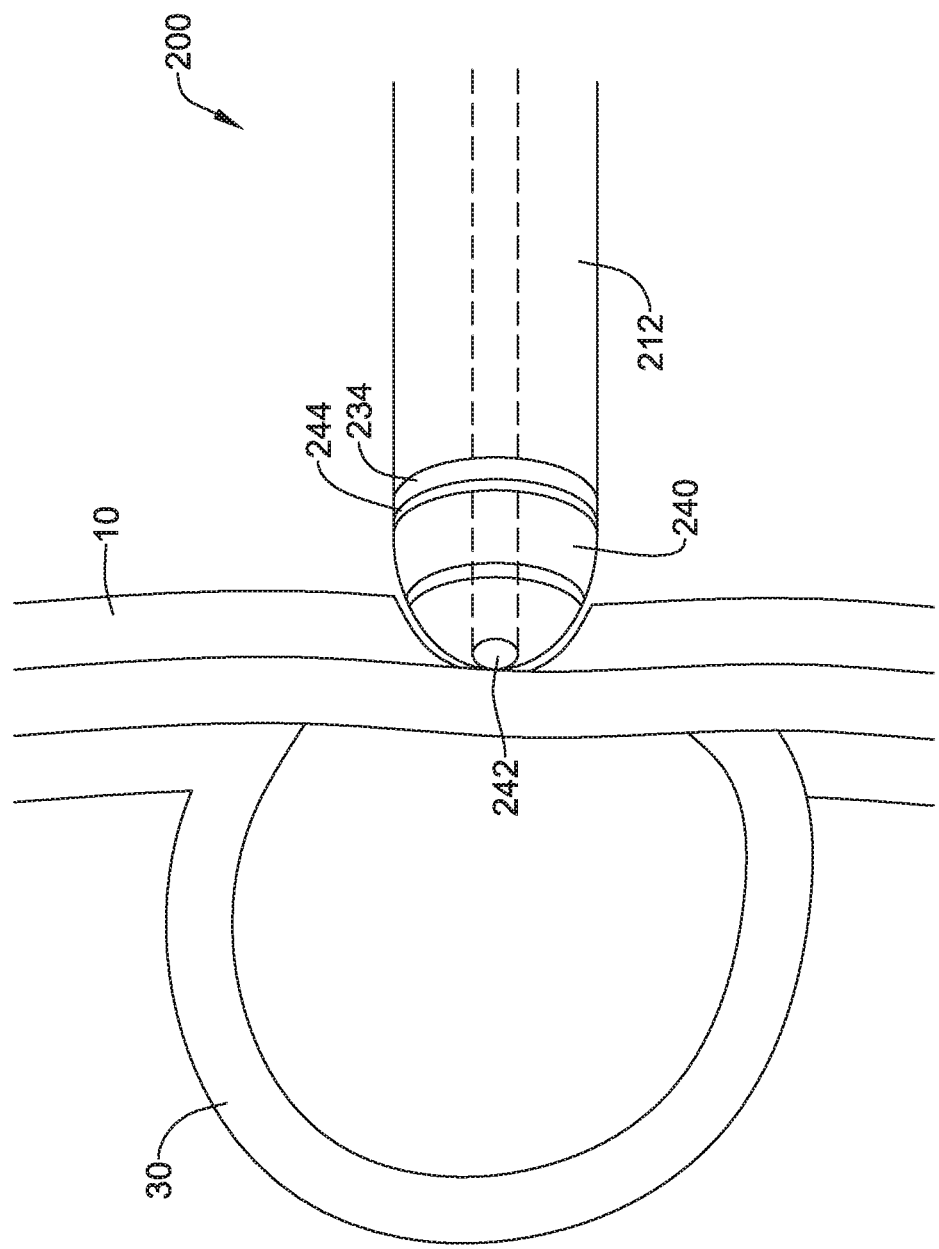
FIG. 5B is an illustration of the catheter of FIG. 4B disposed partially through the pseudocyst wall.
Figure 5C:
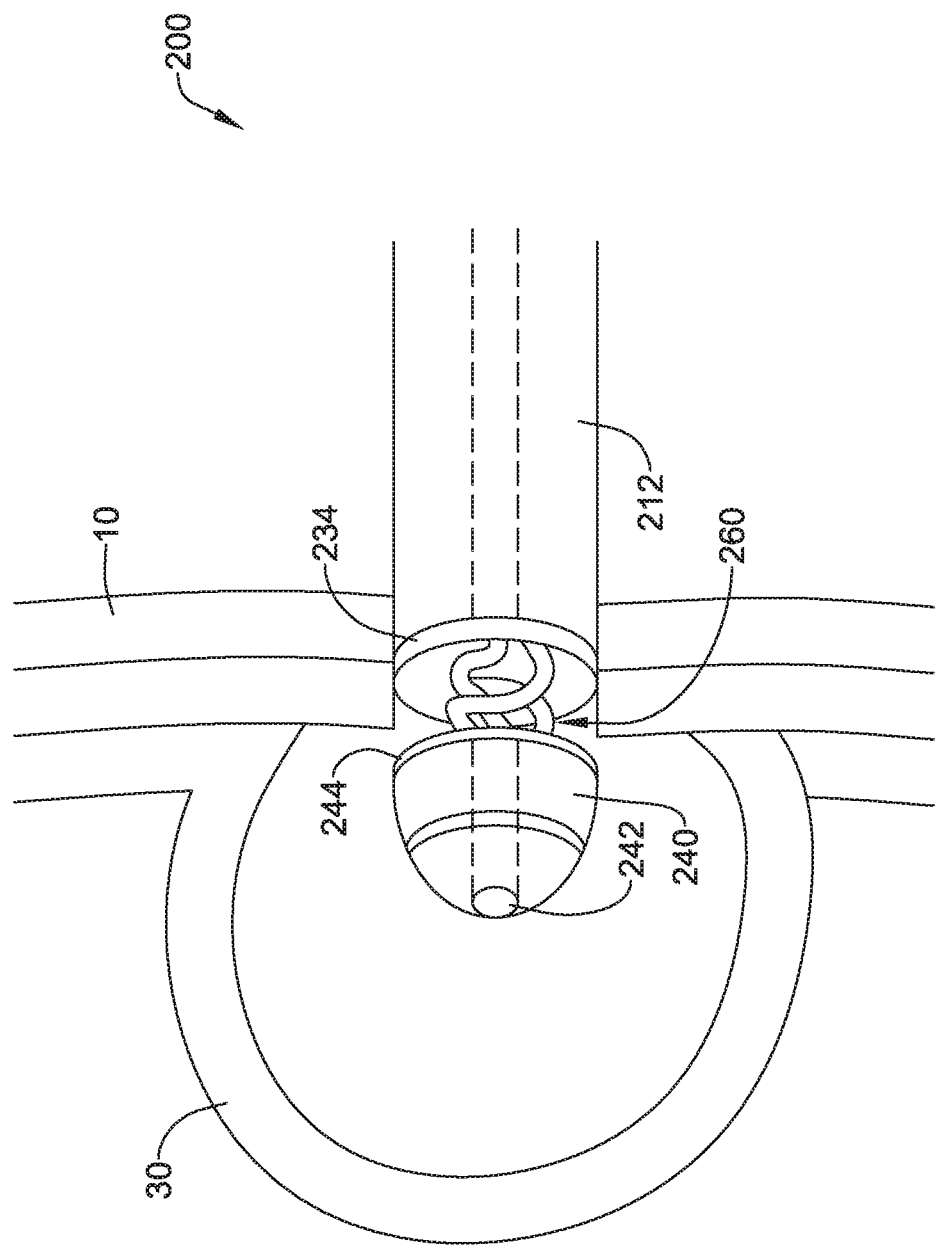
FIG. 5C is an illustration of the catheter of FIG. 4A disposed through the pseudocyst wall.

FIGS. 5A-5C illustrate the cauterization catheter 200 in use. In FIG. 5A, the cauterization catheter 200 is in the first, inactive, position with the distal tip portion 240 spaced apart from the catheter shaft 212. The cauterization catheter 200 is moved into position adjacent the tissue wall 10 abutting the pseudocyst 30 to be drained. As the cauterization catheter 200 is pressed against the tissue wall 10, the spring 260 is compressed and the second contact surface 244 moves into contact with the first contact surface 234, thereby completing the circuit and activating the distal cautery surface 242 to cauterize the tissue wall (FIG. 5B). When the distal tip portion 240 passes through the tissue wall 10 and into the pseudocyst 30, the pressure on the distal tip portion 240 is reduced or eliminated, allowing the spring 260 to expand, breaking the circuit (FIG. 5C). The spring 260 may provide an automatic breaking of the circuit and termination of cauterization as soon as the distal tip portion 240 enters the pseudocyst 30, preventing accidental cauterization of the back wall of the pseudocyst. This may allow the cauterization catheter 200 to be used to drain small pseudocysts or to place stents across the walls of small lumens.

Figure 6A:
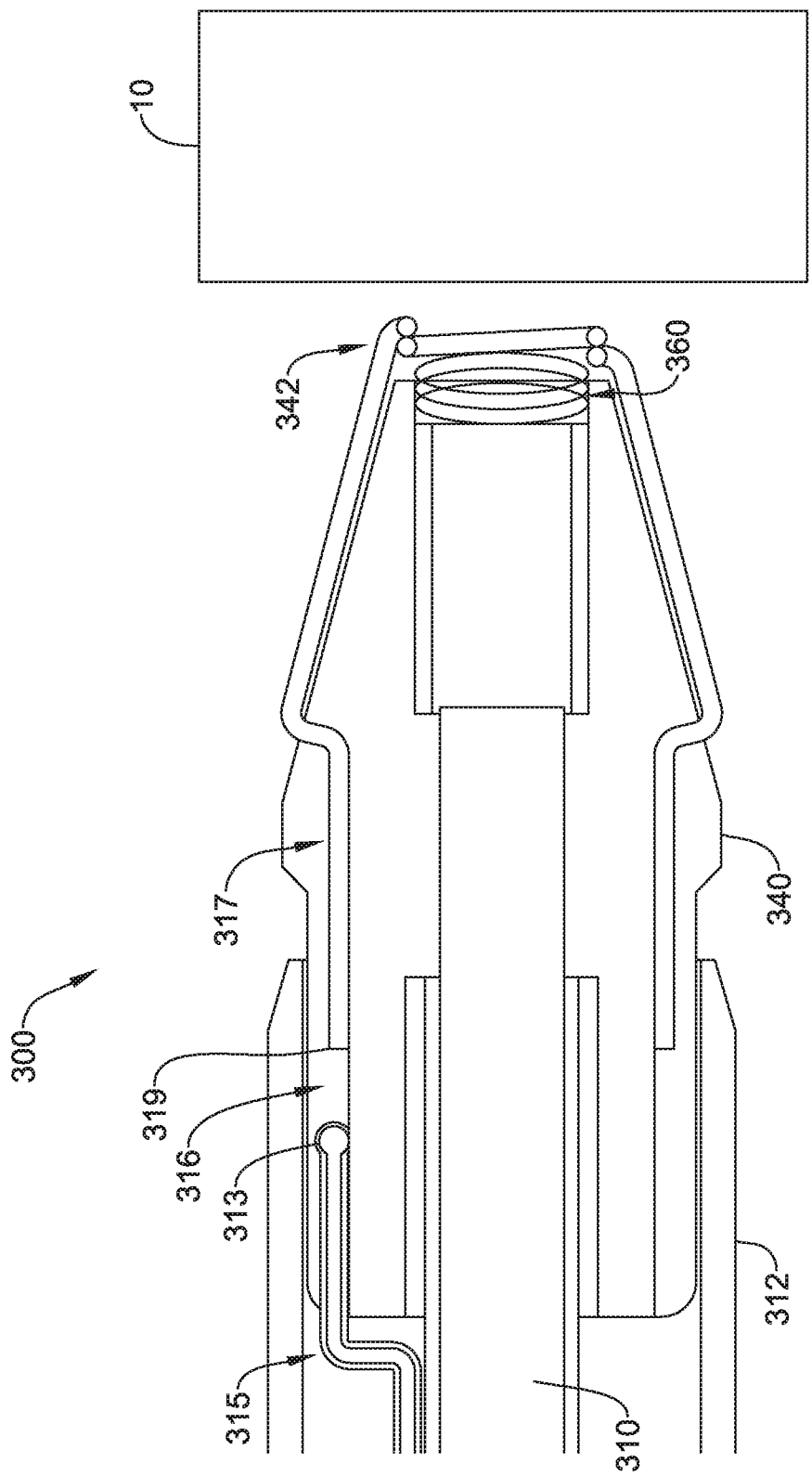
FIG. 6A is a cross-sectional view of a third exemplary cauterization catheter in a first position adjacent a tissue wall.
Figure 6B:
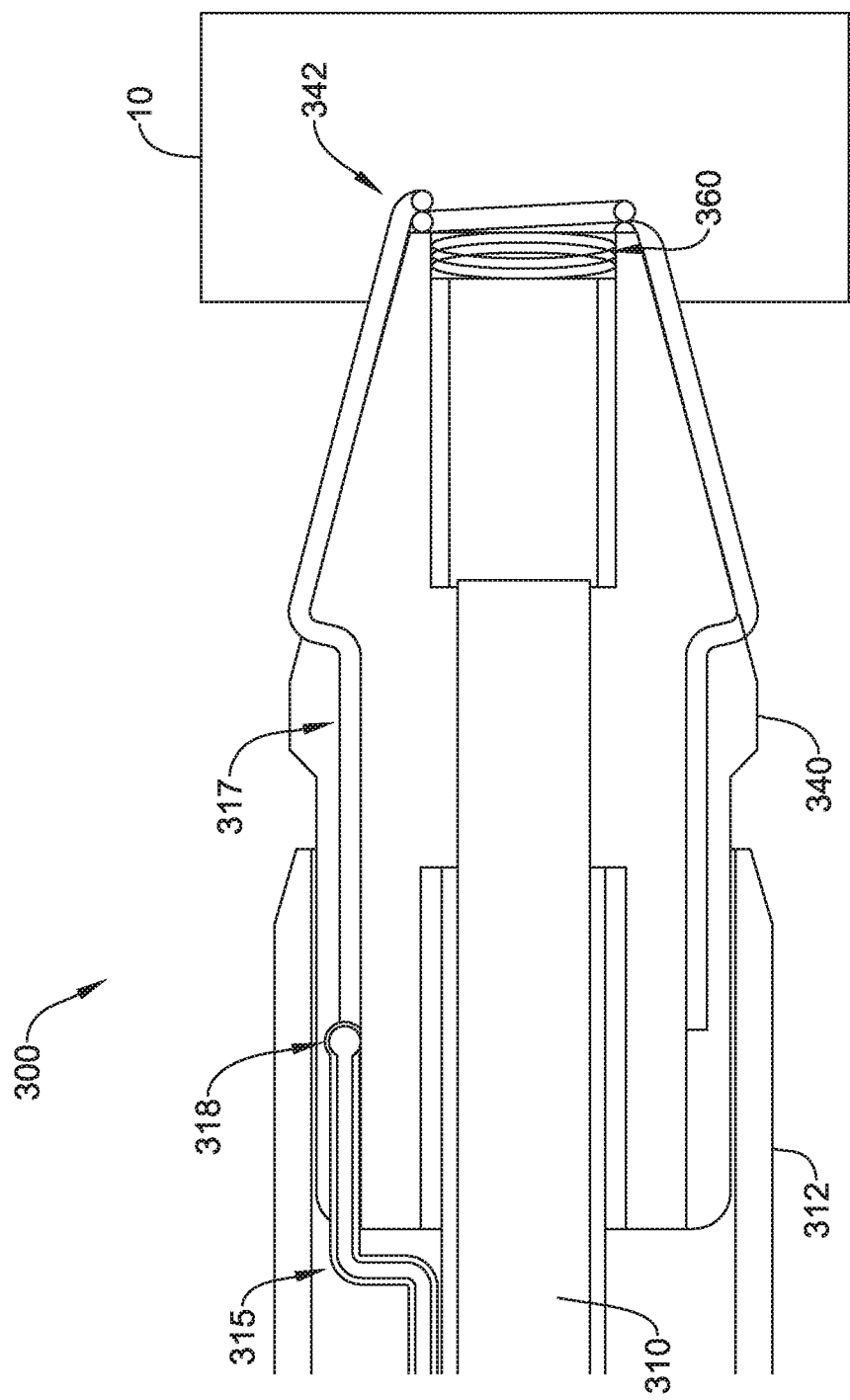
FIG. 6B is a cross-sectional view of the catheter of FIG. 6A in a second position partially within the tissue wall.
Figure 6C:
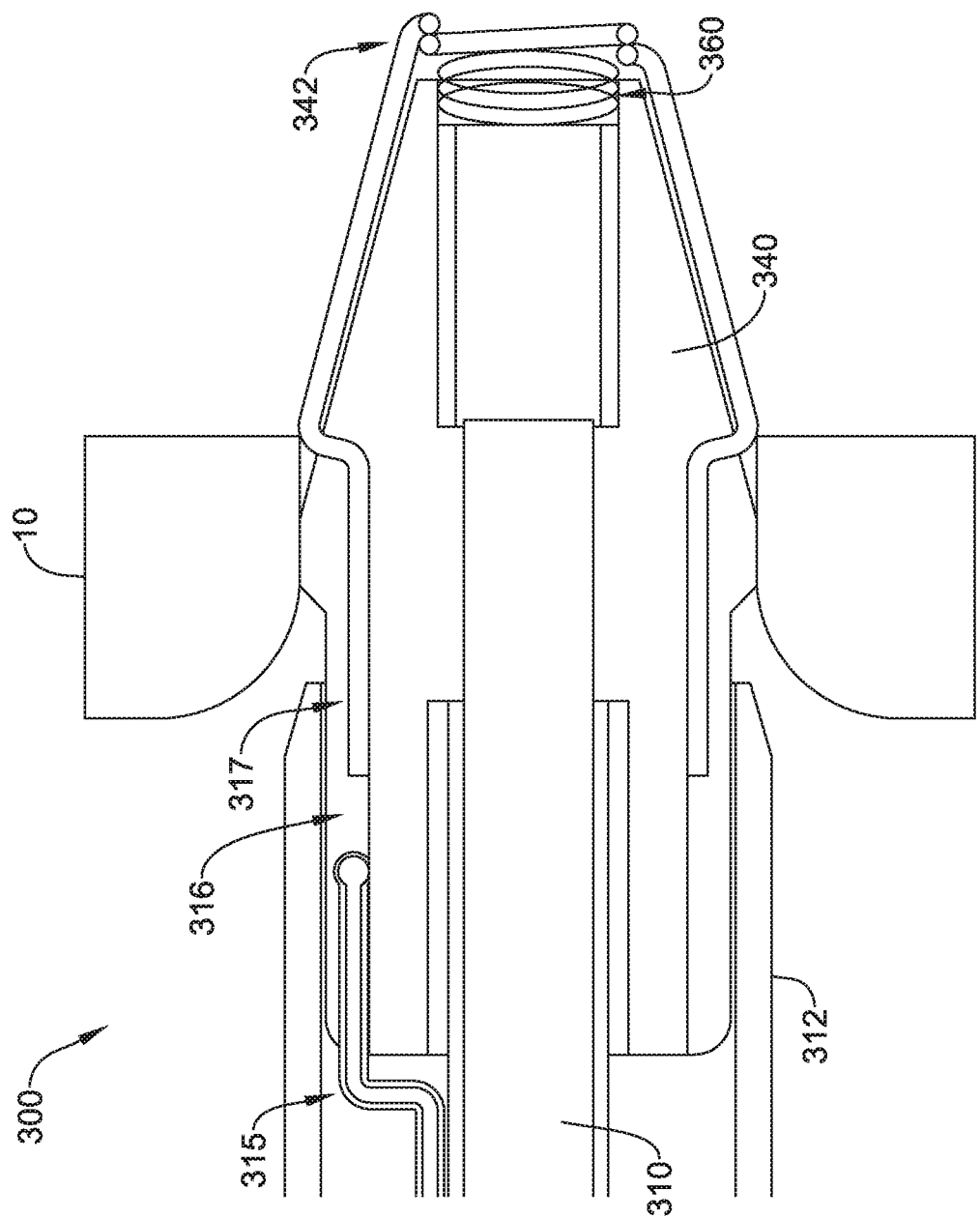
FIG. 6C is a cross-sectional view of the catheter of FIG. 6A in the first position disposed through the tissue wall.

FIGS. 6A-6C illustrate a further exemplary cauterization catheter 300. In this example, the cauterization catheter 300 may include an inner shaft 310, an outer shaft 312, and a first electrically conductive wire 315 extending through the outer shaft 312. The first wire distal end 313 may be positioned proximal of the distal end of the outer shaft 312. The cauterization catheter 300 may further include a distal tip portion 340 at least partially disposed within the outer shaft 312 and over the inner shaft 310. The distal tip portion 340 may have a second electrically conductive wire 317 extending to a distal cautery surface 342. The second wire proximal end 319 may be spaced apart from the first wire distal end 313 by a gap 316. The distal tip portion 340 may include a spring 360 disposed between a distal end of the inner shaft 310 and the distal cautery surface 342. The distal tip portion 340 may be slidable within the outer shaft 312 upon application of a proximally directed force on the distal cautery surface 342. The distal tip portion 340 may be moveable between a first, inactive position, shown in FIG. 6A, and a second, active position, shown in FIG. 6B. In the first, inactive position, the first and second wires 315, 317 are spaced apart by the gap 316, breaking the electrical circuit formed by the first and second wires 315, 317. The distal cautery surface 342 is inactive.

Pressing the cauterization catheter 300 against the tissue wall 10 causes the spring 360 to compress, moving the distal tip portion 340 proximally which moves the second wire 317 into contact with the first wire 315 at contact point 318, thereby completing the circuit and activating the distal cautery surface 342 to cauterize the tissue wall (FIG. 6B). When a majority of the distal tip portion 340 passes through the tissue wall 10, the reduction or elimination of pressure on the distal cautery surface 342 causes the spring 360 to expand, moving the second wire 317 distally away from the first wire 315 and breaking the circuit, stopping cauterization (FIG. 6C).

Figure 7A:
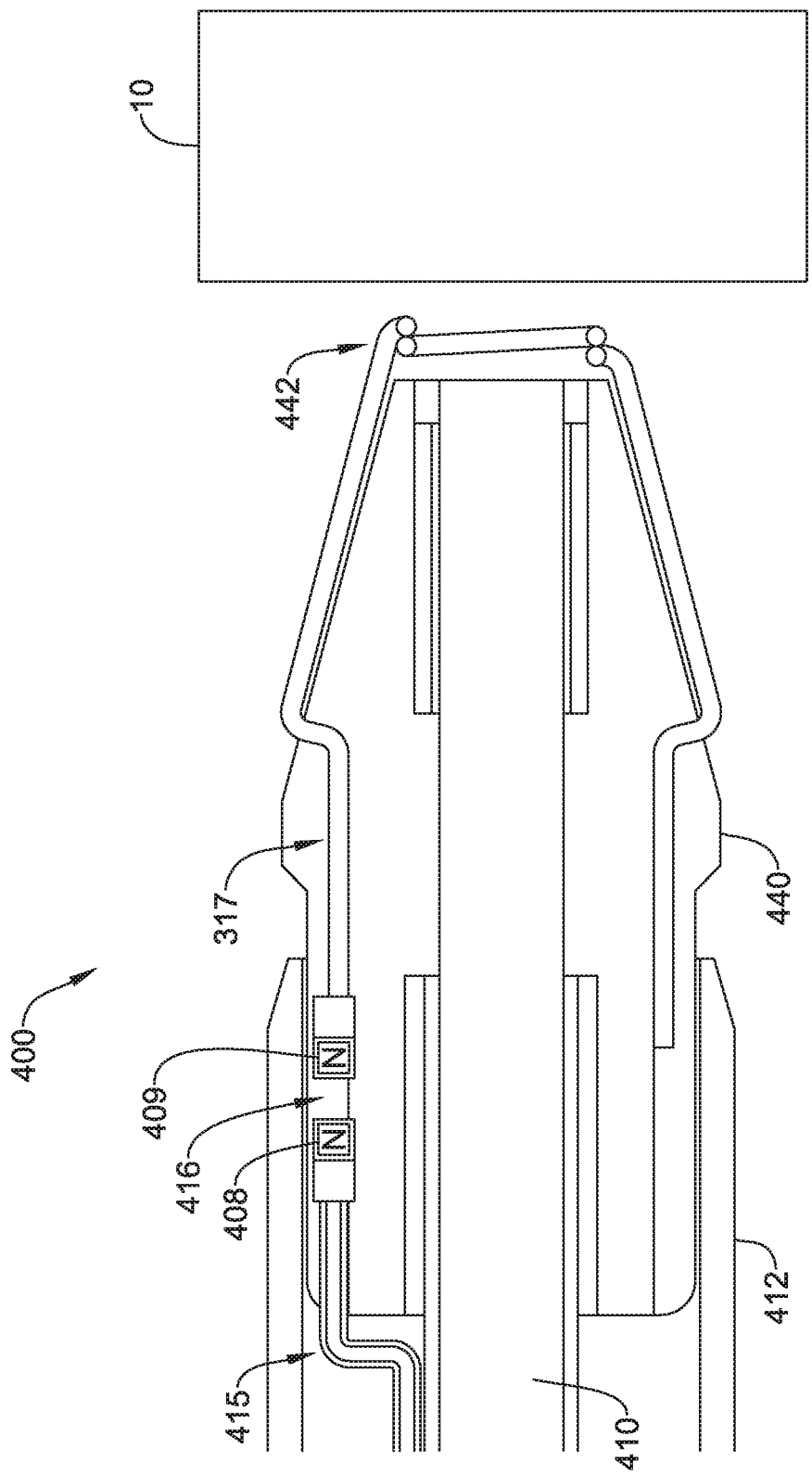
FIG. 7A is a cross-sectional view of a fourth exemplary cauterization catheter in a first position adjacent a tissue wall.
Figure 7B:
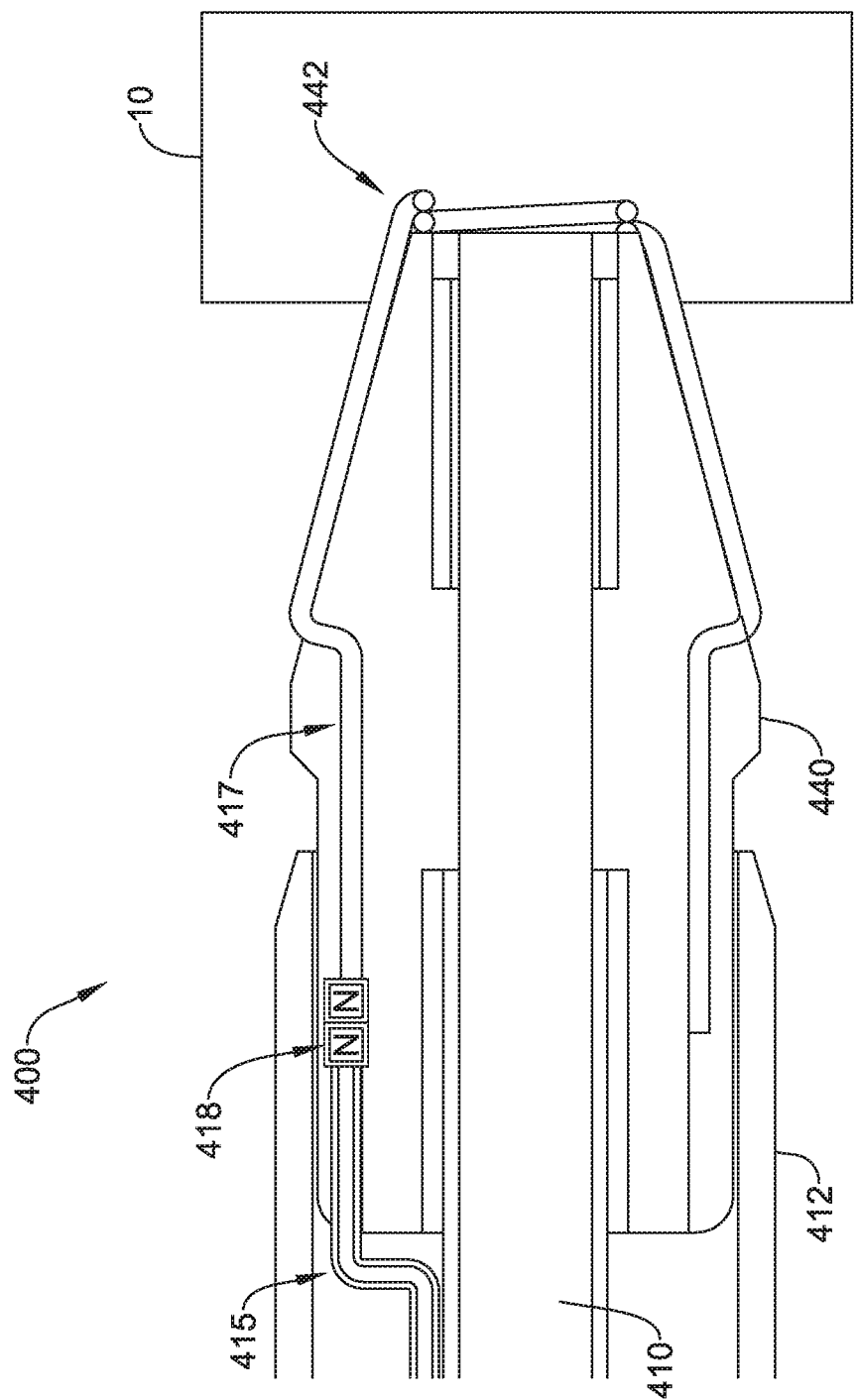
FIG. 7B is a cross-sectional view of the catheter of FIG. 7A in a second position partially within the tissue wall.

FIGS. 7A and 7B illustrate another exemplary cauterization catheter 400 that involves magnets to maintain the device in the first, inactive position. The cauterization catheter 400 may include an inner shaft 410, an outer shaft 412, and a first electrically conductive wire 415 extending through the outer shaft 412. A first magnet 408 may be disposed at the distal end of the first wire, with the first magnet 408 positioned proximal of the distal end of the outer shaft 412. The cauterization catheter 400 may further include a distal tip portion 440 at least partially disposed within the outer shaft 412 and over the inner shaft 410. The distal tip portion 440 may have a second electrically conductive wire 417 extending to a distal cautery surface 442. The second wire 417 may have a second magnet 409 disposed at a proximal end thereof. The first magnet 408 and the second magnet 409 may be oriented with similar poles facing each other such that the magnets repel one another when in close proximity, creating a gap 416 between the magnets. The first and second magnets 408, 409 bias the cauterization catheter 400 in the first, inactive position, shown in FIG. 7A, with the first and second wires 415, 417 spaced apart by the gap 416, breaking the electrical circuit formed by the first and second wires 415, 417. The distal cautery surface 442 is inactive.

Pressing the cauterization catheter 400 against the tissue wall 10 provides a proximally directed force on the distal cautery surface 442. This force overcomes the repelling force of the first and second magnets 408, 409, allowing the distal tip portion 440 to slide proximally within the outer shaft 412 and moving the second wire 417 into contact with the first wire 415 at contact point 418, thereby completing the circuit and activating the distal cautery surface 442 to cauterize the tissue wall (FIG. 7B). When a majority of the distal tip portion 440 passes through the tissue wall 10, the pressure on the distal tip portion 440 is reduced or eliminated, allowing the repelling force of the first and second agents 408, 409 to move the second wire 417 away from the first wire 415, breaking the circuit and moving the cauterization catheter 400 back into the first, inactive position.

Figure 8A:
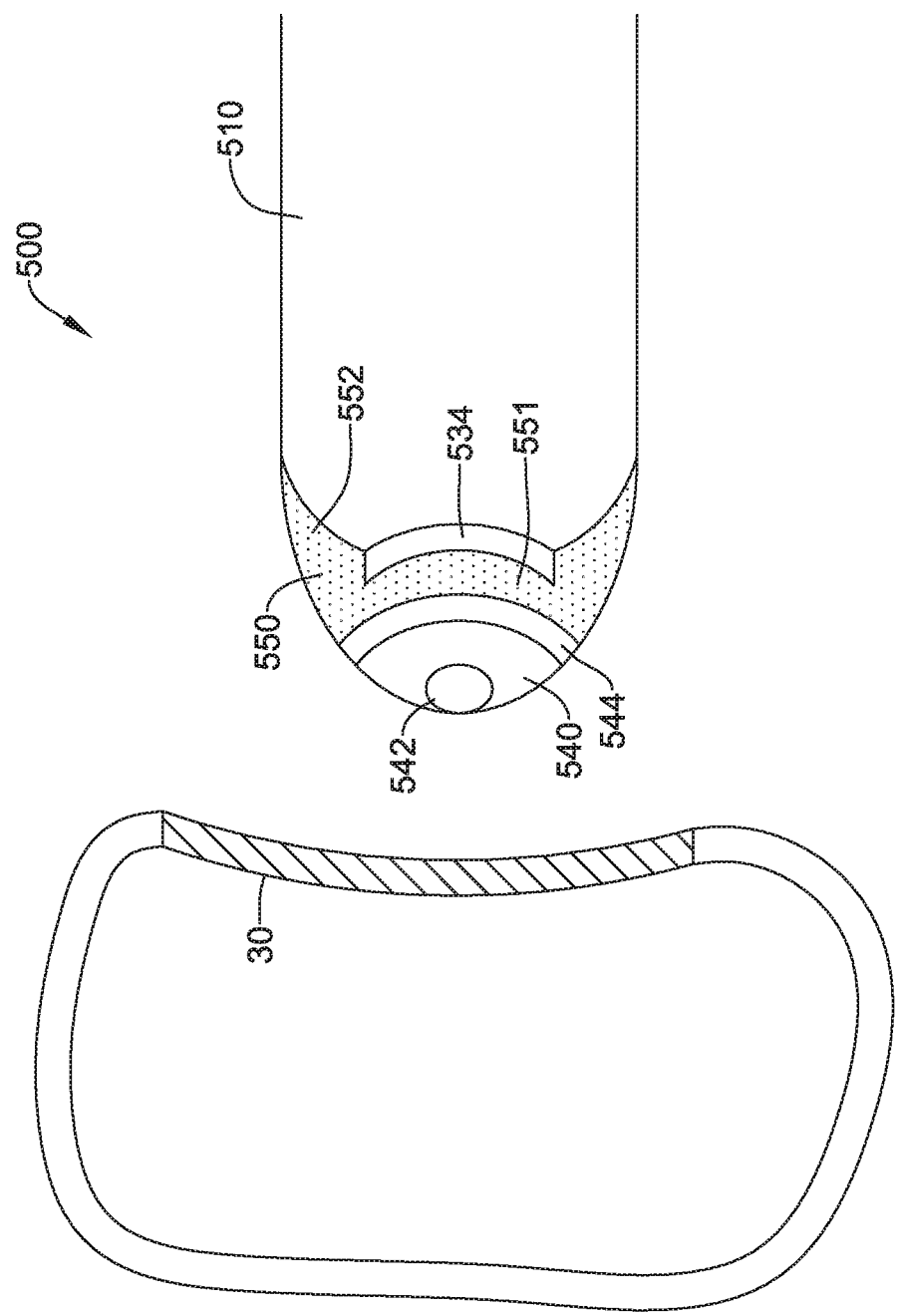
FIG. 8A is a cross-sectional view of a fifth exemplary cauterization catheter in a first position adjacent a tissue wall.
Figure 8B:
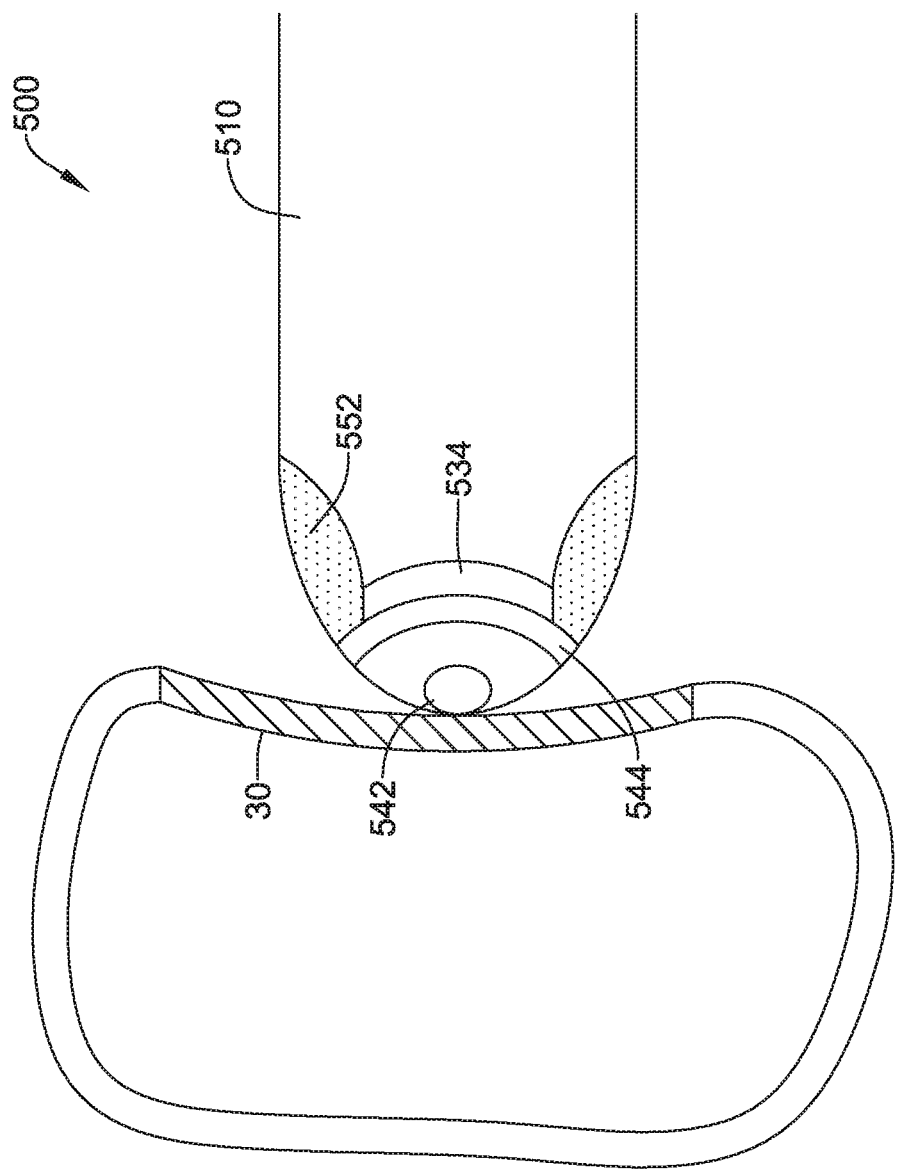
FIG. 8B is a cross-sectional view of the catheter of FIG. 8A in a second position partially within the tissue wall.
Figure 8C:
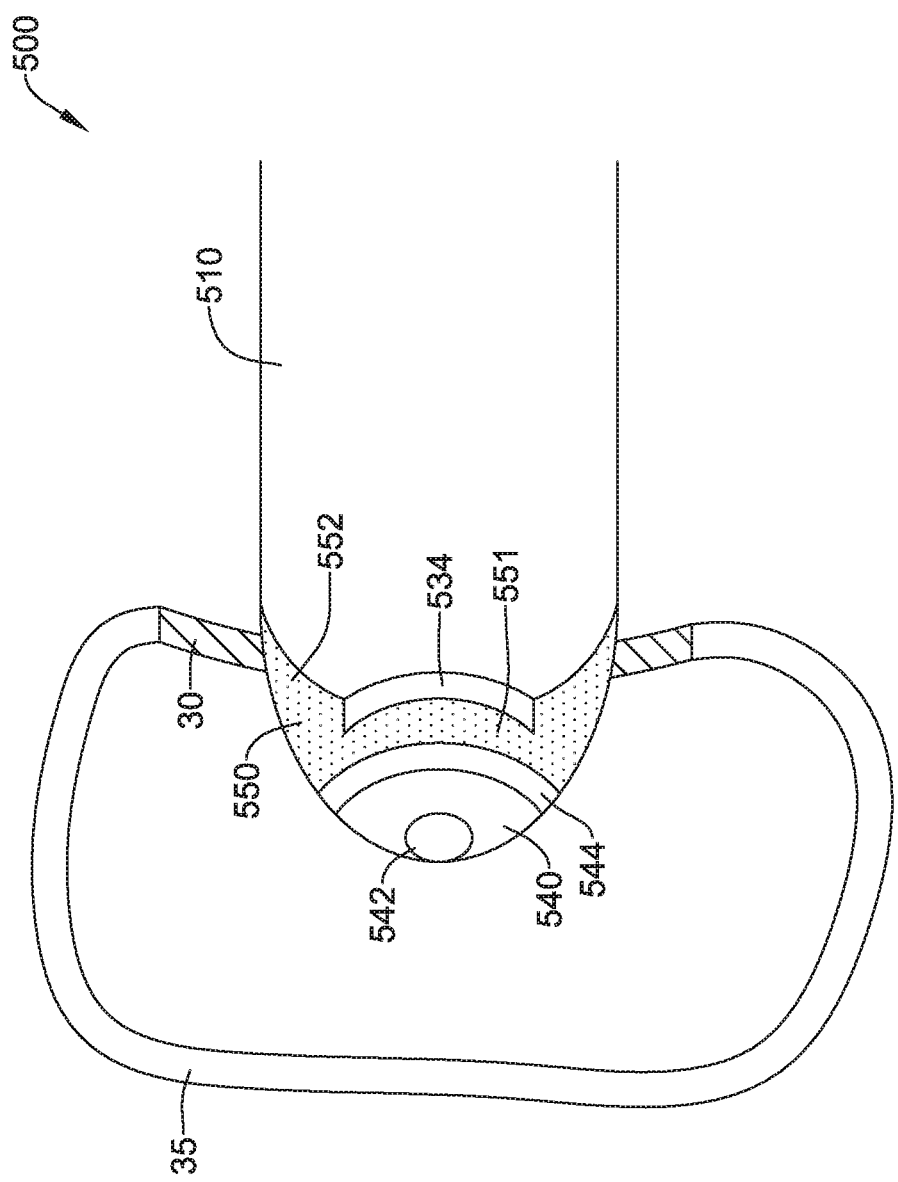
FIG. 8C is a cross-sectional view of the catheter of FIG. 8A in the first position disposed through the tissue wall.

FIGS. 8A-8C illustrate another exemplary cauterization catheter 500. In this example, the cauterization catheter 500 may include a catheter shaft 510 having a first electrical contact surface 534, a distal tip portion 540 having a second electrical contact surface 544, and a fluid filled chamber 550 disposed between the first and second electrical contact surfaces 534, 544. The walls of the catheter shaft 510 in the region of the chamber 550 may be at least partially compressible, allowing the distal tip portion 540 to move proximally relative to the catheter shaft 510. The distal tip portion 540 may include a distal cautery surface 542 electrically connected to the second electrical contact surface 544. The fluid filled chamber 550 biases the cauterization catheter 500 in the first, inactive position, holding the first and second electrical contact surfaces 534, 544 apart from one another, breaking the electrical circuit, as shown in FIG. 8A. The fluid filled chamber 550 may have a first portion 551 disposed between the first and second electrical contact surfaces 534, 544, and a second portion 552 disposed proximal of the first electrical contact surface 534. The fluid within the chamber 550 may pass freely between the first and second portions 551, 552. When at equilibrium (no force acting on the distal tip portion 540), the fluid is evenly distributed between the first and second portions 551, 552. A proximally directed force exerted on the distal tip portion 540 compresses and/or collapses the first portion 551 of the chamber, forcing fluid out of the first portion 551 and into the second portion 552. As the first portion 551 is compressed and/or collapsed, the second contact surface 544 contacts the first contact surface 534, completing the electrical circuit and activating the distal cautery surface 542, as shown in FIG. 8B. In this second position the distal cautery surface 542 is activated, allowing the surface to cut through a tissue wall or pseudocyst 30 to be drained. When the distal tip portion 540 passes into the pseudocyst 30, the pressure on the distal tip portion 540 is reduced or eliminated, allowing the fluid to move back into the first portion 551 of the chamber, reaching equilibrium and separating the first and second electrical contact surfaces 534, 544, breaking the circuit (FIG. 8C).

Although only illustrated in FIG. 3A with respect to the first exemplary cauterization catheter 100, it will be understood that any of the exemplary cauterization catheters 100, 200, 300, 400, 500 may be used to deliver a stent 600 across a lumen wall or pseudocyst wall.

In some embodiments, the electrically conductive cautery wires 115, 315, 317, 415, 417, electrical contact surfaces 144, 234, 244, 534, 544, and distal cautery surfaces 142, 242, 342, 442, 542 may be formed of titanium or titanium alloys, stainless steel alloys, copper or copper alloys, silver or silver alloys, gold or gold alloys, platinum or platinum alloys, tungsten or tungsten alloys, magnesium or magnesium alloys, carbon or carbon alloys, or nickel alloys such as nickel-chromium-molybdenum alloys (e.g., UNS: N06625 such as INCONEL® 625). However, in some embodiments, other conductive materials may be used to form the electrically conductive wires.

In some embodiments, the catheter components such as the outer shaft 112, 212, 312, 412, 510, proximal cautery portion 130, and distal cautery portion 140, 240, 340, 440, 540 may be formed of polyamide, polyethylene, polypropylene, polystyrene, polyurethane, polyethylene, nylon, polycarbonate, fluoroplastic, fluoropolymer, thermoplastic elastomer such as C-FLEX®, a thermoplastic polyurethane elastomer such as TECOTHANE®, TECOFLEX® or TEXIN®, a thermoplastic polyester elastomer such as HYTREL®, or a mixture, a blend or a co-polymer thereof.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A lumen-apposing access system comprising:
   a catheter having a proximal end and a distal end; and
   a cauterization tip disposed on the distal end of the catheter, the cauterization tip having a proximal portion, a distal portion having a tapered distal tip portion, and a biasing member positioned within the tapered distal tip portion, the distal portion including a cautery element, wherein the distal portion includes a proximal neck slidingly disposed within a lumen of the proximal portion during use between a first position in which the cautery element is electrically inactive, and a second position in which the cautery element is electrically active, wherein the biasing member biases the distal portion in the first position;
   wherein the biasing member is a helical spring having a plurality of helical windings.

2. The access system of claim 1, wherein when in the first position, the distal portion is spaced apart from the proximal portion and when in the second position, the distal portion contacts the proximal portion.

3. The access system of claim 2, wherein the cauterization tip includes an electrical circuit that is completed when the distal portion is in the second position, and the electrical circuit is broken when the distal portion is in the first position.

4. The access system of claim 3, wherein a wire extends through the catheter from the proximal end to the proximal portion of the cauterization tip, wherein the distal portion has a contact surface that contacts the wire when the distal portion is in the second position, completing the electrical circuit, and is spaced apart from the wire when the distal portion is in the first position.

5. The access system of claim 1, wherein a proximal end of the distal portion and a distal end of the proximal portion include electrical contacts.

6. The access system of claim 1, wherein a first wire extends through the catheter from the proximal end to the proximal portion of the cauterization tip, wherein the distal portion has a second wire extending from a distal tip cautery surface into the proximal neck, wherein when the spring is in a relaxed state and the distal portion is in the first position, the second wire is spaced apart from the first wire, wherein when the spring is compressed and the distal portion is in the second position, the second wire contacts the first wire, completing an electrical circuit between the first wire and the second wire.

7. The access system of claim 1, wherein a first wire extends through the catheter from the proximal end to the proximal portion of the cauterization tip, wherein a second wire extends through the distal portion from the distal tip portion to the proximal portion, wherein the second wire contacts the first wire when the distal portion is in the second position, completing the electrical circuit, and the second wire is spaced apart from the first wire when the distal portion is in the first position.

8. The access system of claim 1, wherein the cautery element is movable relative to the tapered distal tip portion.

9. The access system of claim 1, wherein when a proximally directed force is applied to a distal end of the distal portion, the biasing member is compressed and the distal portion moves from the first position to the second position.

10. A lumen-apposing access system comprising:
- a catheter having a proximal end and a distal end;
- an inner shaft axially moveable within a lumen of the catheter; and
- a cauterization tip disposed on a distal end of the inner shaft, the cauterization tip having a proximal portion, a distal portion having a tapered distal tip portion, and a biasing member positioned within the tapered distal tip portion, the distal portion extending distal of the distal end of the catheter and including a cautery element, wherein the distal portion includes a proximal neck slidingly disposed within a lumen of the proximal portion during use between a first position in which the cautery element is electrically inactive, and a second position in which the cautery element is electrically active, wherein the biasing member biases the distal portion in the first position;
- wherein the biasing member is a helical spring having a plurality of helical windings.

11. The access system of claim 10, wherein a wire extends along the inner shaft from the proximal end of the catheter to the proximal portion of the cauterization tip, wherein the distal portion has a contact surface that contacts the wire when the distal portion is in the second position, completing an electrical circuit, and is spaced apart from the wire when the distal portion is in the first position, breaking the electrical circuit.

12. The access system of claim 10, wherein the cautery element is movable relative to the tapered distal tip portion.

13. A lumen-apposing access system comprising:
- a catheter having a proximal end and a distal end; and
- a cauterization tip disposed on the distal end of the catheter, the cauterization tip having a proximal portion, a distal portion having a tapered distal tip portion, and a biasing member positioned within the tapered distal tip portion, the distal portion including a cautery element, wherein the distal portion includes a proximal neck slidingly disposed within a lumen of the proximal portion during use between a first position in which the cautery element is electrically inactive, and a second position in which the cautery element is electrically active, wherein the biasing member biases the distal portion in the first position;
- wherein the biasing member is a helical spring having a plurality of helical windings; and
- wherein when a proximally directed force is applied to a distal end of the distal portion, the biasing member is compressed and the distal portion moves from the first position to the second position.

14. The access system of claim 13, wherein the cautery element is movable relative to the tapered distal tip portion.

15. The access system of claim 13, wherein when the proximally directed force is removed from the distal end of the distal portion, the biasing member expands and the distal portion moves from the second position to the first position.

* * * * *